(12) United States Patent
Adams et al.

(10) Patent No.: US 6,453,007 B2
(45) Date of Patent: Sep. 17, 2002

(54) X-RAY INSPECTION USING CO-PLANAR PENCIL AND FAN BEAMS

(75) Inventors: William L. Adams, Powell, OH (US); Lee Grodzins, Lexington, MA (US)

(73) Assignee: American Science and Engineering, Inc., Billerica, MA (US)

( * ) Notice: Subject to any disclaimer, the term of this patent is extended or adjusted under 35 U.S.C. 154(b) by 6 days.

(21) Appl. No.: 09/785,672

(22) Filed: Feb. 16, 2001

Related U.S. Application Data

(63) Continuation-in-part of application No. 09/448,717, filed on Nov. 24, 1999, now Pat. No. 6,192,104.
(60) Provisional application No. 60/110,223, filed on Nov. 30, 1998, and provisional application No. 60/134,413, filed on May 17, 1999.

(51) Int. Cl.⁷ .............................................. G01N 23/04
(52) U.S. Cl. ........................... 378/90; 378/57; 378/146; 378/160
(58) Field of Search ............................ 378/57, 90, 146, 378/147, 149, 160

(56) References Cited

U.S. PATENT DOCUMENTS

| | | | | |
|---|---|---|---|---|
| 5,179,581 A | * | 1/1993 | Annis | 378/57 |
| 5,600,700 A | * | 2/1997 | Krug et al. | 378/57 |
| 5,666,393 A | * | 9/1997 | Annis | 378/57 |
| 5,930,326 A | * | 7/1999 | Rothschild et al. | 378/57 |
| 6,151,381 A | * | 11/2000 | Grodzins et al. | 378/90 |
| 6,192,104 B1 | * | 2/2001 | Adams et al. | 378/90 |

* cited by examiner

Primary Examiner—Robert H. Kim
Assistant Examiner—Allen C. Ho
(74) Attorney, Agent, or Firm—Bromberg & Sunstein LLP

(57) ABSTRACT

An inspection system is for inspecting an object with penetrating radiation. A source of penetrating radiation provides a beam of radiation. The beam alternates between a first beam shape and a second beam shape, the first and second beam shapes being coplanar. A first detector arrangement is for detecting penetrating radiation from a portion of the beam transmitted through the object and generating a transmitted radiation signal. A second detector arrangement is for detecting penetrating radiation from a portion of the beam scattered by the object and generating a scattered radiation signal. A processor determines at least one characteristic of the object based at least on the transmitted and scattered radiation signals.

26 Claims, 3 Drawing Sheets

X-RAY INSPECTION USING CO-PLANAR PENCIL AND FAN BEAMS

This application is a continuation-in-part of U.S. patent application Ser. No. 09/448,717, filed Nov. 24, 1999, now U.S. Pat. No. 6,192,104, which in turn claimed priority from U.S. provisional patent applications No. 60/110,223, filed Nov. 30, 1998, and No. 60/134,413, filed May 17, 1999, all of which are incorporated herein by reference.

FIELD OF THE INVENTION

The present invention relates to inspecting an object with penetrating radiation using both fan-shaped and pencil-shaped beams, which are scanned successively across the inspected object.

BACKGROUND ART

Penetrating radiation, such as X-rays, is often used for the inspection of enclosures such as cargo containers. The use of x-rays both transmitted through the inspected item and scattered by its contents is known in the art. Typically, the item is illuminated by a single source of x-rays, from which transmitted and scattered radiation are detected by detectors or arrays of detectors that are disposed, respectively, in the direction of propagation of the illuminating beam or in other directions, to the front, back, or sides of the inspected item.

U.S. Pat. No. 6,151,381, incorporated herein by reference, describes a penetrating radiation-based inspection system. A pencil-shaped beam of radiation is described for backscattered detection imaging. A fan-shaped beam of radiation is described for imaging the contents of an enclosure on the basis of radiation transmitted through the enclosure. Commonly assigned application Ser. No. 09/448,717 U.S. Pat. No. 6,192,104, describes such a system using a single source of radiation to produce non-coplanar pencil and fan beams.

SUMMARY OF THE INVENTION

A representative embodiment of the present invention includes an inspection system and method for inspecting an object with penetrating radiation. A source of penetrating radiation provides a beam of radiation. The beam alternates between a first beam shape and a second beam shape, the first and second beam shapes being coplanar. A first detector arrangement is for detecting penetrating radiation from a portion of the beam transmitted through the object and generating a transmitted radiation signal. A second detector arrangement is for detecting penetrating radiation from a portion of the beam scattered by the object and generating a scattered radiation signal. A processor determines at least one characteristic of the object based at least on the transmitted and scattered radiation signals.

The source of penetrating radiation may be an x-ray source, for example, a continuous or pulsed x-ray source from an x-ray tube. Alternatively, the source of penetrating radiation may be a linear accelerator. The beam shapes may be determined by a rotating chopper wheel, or by a rotating disk and slit arrangement. The first beam shape may be a pencil-shape, and the second beam shape may be a fan-shape. A collimator may be used for producing the fan shape. An absorber may reduce the intensity of low-energy components of the beam, while not significantly affecting the intensity of high-energy components of the beam. A scanner arrangement may be used for varying the orientation of the pencil shape with respect to the object. Either the object may be in motion with respect to the beam, or the system may be in motion with respect to the object.

BRIEF DESCRIPTION OF THE DRAWINGS

The present invention will be more readily understood by reference to the following detailed description taken with the accompanying drawings, in which.

DETAILED DESCRIPTION OF SPECIFIC EMBODIMENTS

Figure 1:
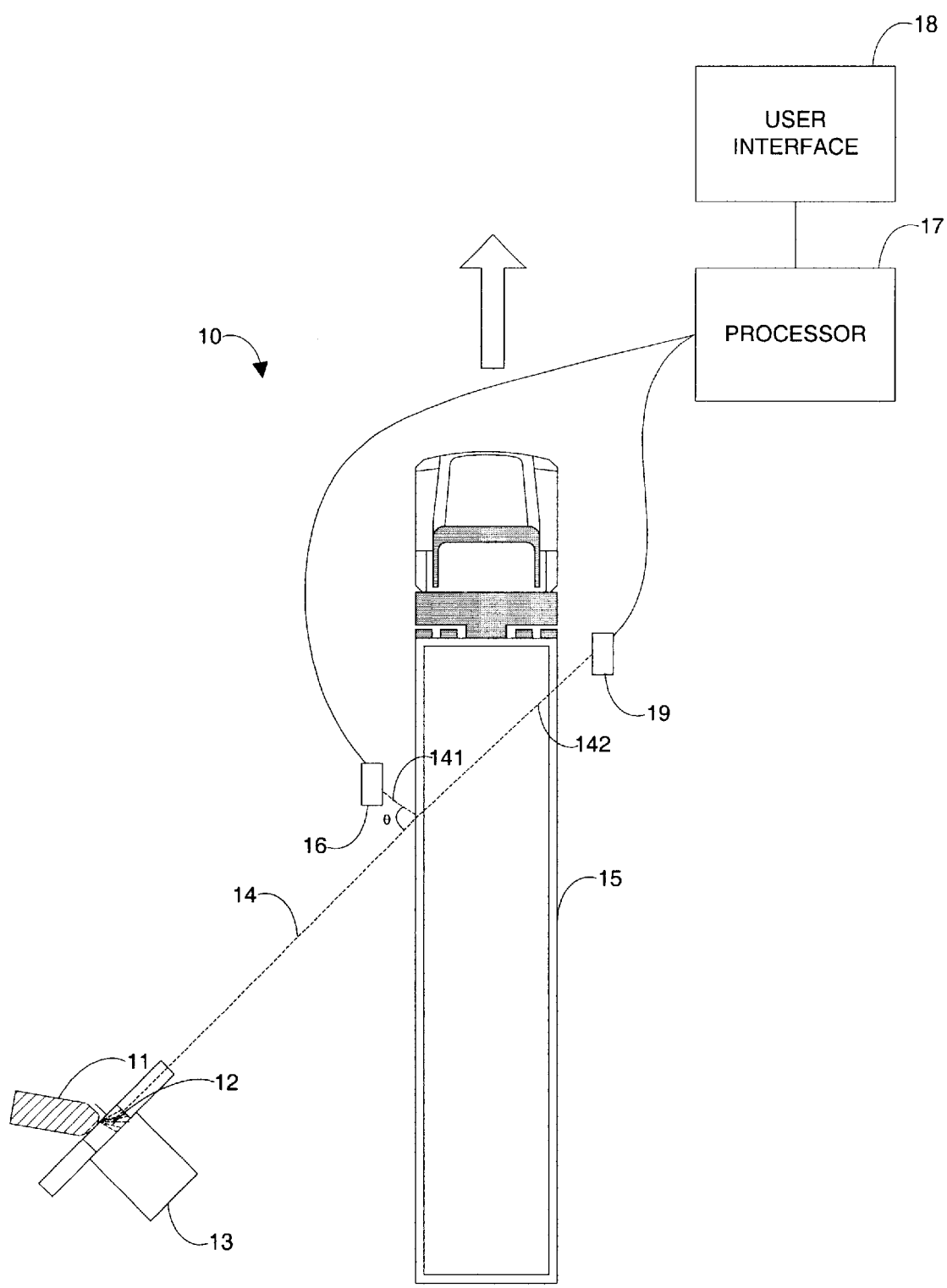
FIG. 1 shows a top view of the elements of a rapid x-ray inspection system.

FIG. 1 shows a top view, according to a representative embodiment, of the elements of a rapid x-ray inspection system, designated generally by numeral 10. A source 11 emits penetrating radiation in a cone-shaped beam 12. Source 11 of penetrating radiation may be a linear accelerator (LINAC), for example, or an x-ray tube, for another example. It is preferred that source 11 be a continuous source of penetrating radiation, such as a CW LINAC, for example. For some applications, a pulsed x-ray generator with an appropriate repetition rate may be used. In a typical arrangement, the source 11 will have an snout-end anode, commonly of tungsten, that generates x-rays. Beam 12 of penetrating radiation, may be, for example, a beam of x-rays such as a polychromatic x-ray beam. Beam 12 will be referred to in the present description, without limitation, as an x-ray beam.

In accordance with one embodiment of the invention, rotating chopper wheel 13 (as described, for example, in U.S. Pat. No. 6,151,381) is used to develop a scanning beam 14, which may be swept in a plane substantially perpendicular to the page, across the inspected object (truck 15 in FIG. 1). The scanning beam 14 may alternate from one shape to another in that transverse plane, e.g., alternating between pencil-shaped and fan-shaped, but the different beam shapes will be confined to the same plane, represented in FIG. 1 by the dashed line of scanning beam 14. When the scanning beam 14 has a pencil-shape, each dimension of the beam is comparable in extent in a substantially rectangular shape. This rectangular shape typically defines a scatter image resolution that may be obtained with the system. When the scanning beam 14 has a fan-shape, the fan has an opening angle in a plane substantially perpendicular to the page. The exact shape of the fan is a matter of design choice, which restricted to a narrow width within the plane of the page by a collimator as described below. The fan shape typically is used to produce a transmission image that may be obtained with the system. The spatial resolution of the transmission image obtained from the fan-shaped beam is determined by the segmentation of the associated array of detectors 19.

Radiation scattered by the inspected object 15 is intercepted by a scatter detector array 16 disposed at some angle θ with respect to the incident scanning beam 14. The energy of the scattered x-ray is generally a substantial fraction of the energy of the incident x-ray and thus the scattered x-ray has considerable penetrating power. When, during the course of rotation of chopper wheel 13, the scanning beam 14 is pencil-shaped, scatter detector array 16 is gated on to detect the scattered beam 141, and forwards the detected signal data to the system processor 17.

In one specific embodiment, the scatter detector array 16 is gated off whenever the scanning beam 14 is not pencil-shaped, so that no scatter signal data is produced or forwarded to the processor 17; for example, when the beam is off or fan-shaped. Alternatively, the scatter detector array 16 also may be gated on when the scanning beam 14 is fan-shaped, so that the scatter data is sent to the processor 17 whenever the scanning beam 14 is on. This additional data is not used for imaging, but it may be useful for signaling the possible presence of bulk objects such as a large quantity of illicit drugs.

A significant portion of the scanning beam 14 is not scattered by the inspected object, but passes substantially straight through the object to transmission detector array 19. Typically, the transmission detector array 19 is gated on when the scanning beam 14 is fan-shaped, in order to gather transmission signal data that, in effect, describes a slice of the inspected object where the beam traverses it. When the transmission detector array 19 is gated on, the transmission signal data is forwarded to the system processor 17. As with the scatter detector array 16, in alternative embodiments the transmission detector array 19 may be gated on whenever the scanning beam 14 is present, regardless of beam shape. For example, detecting an almost unattenuated transmitted scanning beam 14 when it is pencil-shaped would give good sensitivity for lightly loaded cargo in the inspected object 15.

Within the scope of the invention, any x-ray detection technology known in the art may be employed for detector arrays 16 and 19. The transmission detectors 19 may be segmented scintillators or other solid state detectors, for example. Scatter detectors 16 may be any one of a variety of large area detectors including scintillation screens or liquid scintillators which may be doped with tin or other metal. In one embodiment, the transmission detector array 19 may be based on cadmium tungstrate ($CdWO_4$) or cesium iodide (CsI) detectors. The cost of the detector array, which is a function of the total material, is a factor in compromising between spatial resolution and increased penetration.

To scan the entire inspected object 15, it is typical to have the object move slowly forward between the scatter detector array 16 and the transmission detector array 19. For example, a tractor or winch may pull the object 15 forward, or the object 15 may be self-propelled. Alternatively, the object 15 may be kept stationary, and the detector arrays 16 and 19 may be connected on a mobile mechanical structure that slowly moves past the object 15.

The processor 17 processes the scatter and transmission signal data and communicates this processed information to a user interface 18. The user interface 18 also provides a system user with functionality to manipulate the processor 17 to control the processing of the signal data. Typically, the user interface 18 may provide to a system user images of object 15 and its contents. Also, other characteristics of the inspected object 15 may be determined, such as mass, mass density, mass distribution, mean atomic number, or likelihood of containing targeted threat material, all as known to persons skilled in the art of x-ray inspection.

Figure 2:
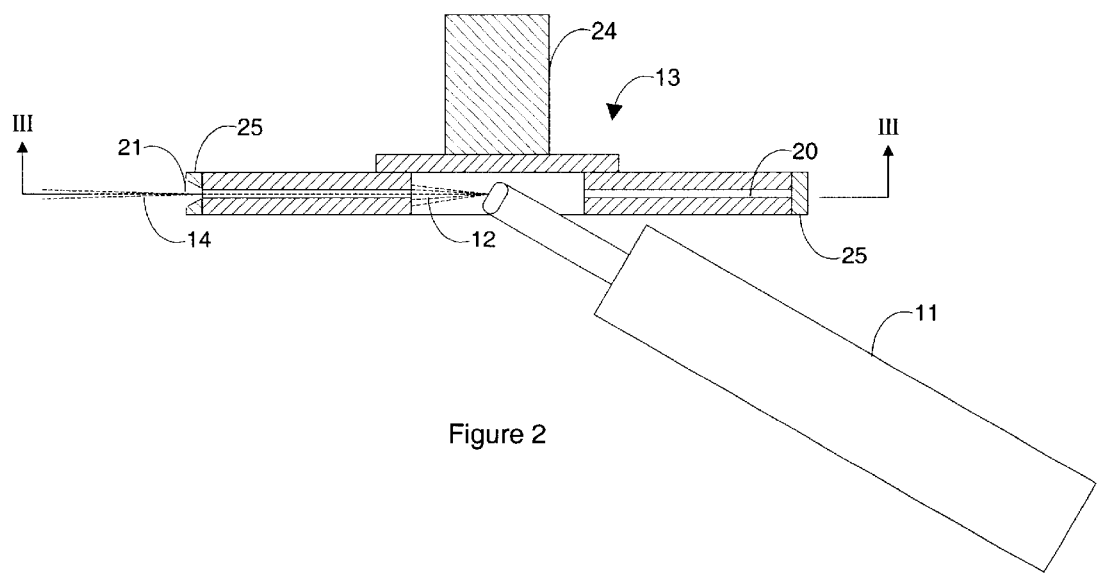
FIG. 2 shows a side cross-section of an arrangement for producing coplanar pencil and fan beams according to one embodiment of the present invention.
Figure 3:
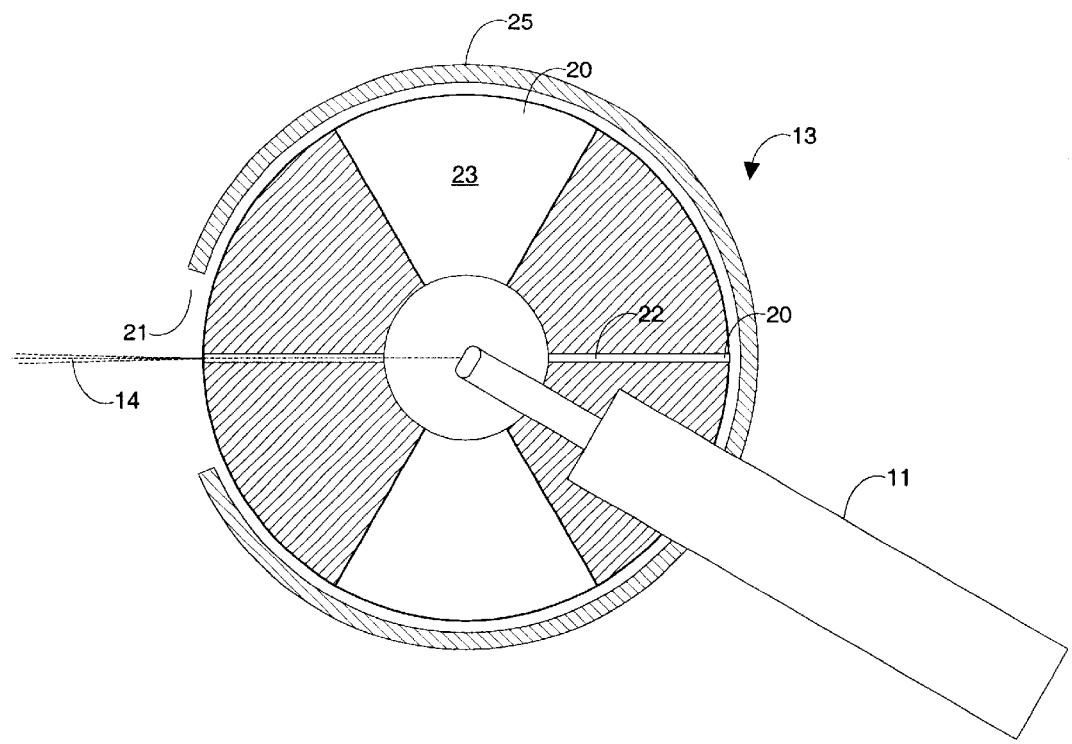
FIG. 3 shows a top cross-section of the arrangement in FIG. 2.

Referring now to FIGS. 2 and 3, greater detail is shown in these views, from above and the side respectively, of the chopper wheel 13 that forms scanning beam 14. The chopper wheel 13, with cavities 22 and 23, is made in part of an x-ray absorbing material such as lead, and is rotated by a rotary actuator such as driving motor 24. The scanning beam 14 is formed by the chopper wheel 13 from the x-ray beam 12 emitted by the radiation source 11. Segmental cavities 20 within the rotating chopper wheel 13 act as beam collimators to shape the scanning beam 14. The chopper wheel assembly 13 has an outer tube 25 of x-ray absorbing material, such as lead. The tube 25 has a beam opening 21 that allows x-ray radiation within an aligned one of the rotating cavities 20 to project out from the chopper wheel 13 as the scanning beam 14. A columnar spoke-shaped cavity 22 produces a pencil-shaped scanning beam 14 when it rotates across the beam opening 21. A slit pie-shaped cavity 23 produces a fan-shaped scanning beam 14 when it rotates across the beam opening 21. One issue is the potential for undesired increased ambient radiation. One potential solution is to add a radiation absorber to the beam opening 21 to use shaped energy. An alternative is to add a radiation absorber only to the pie-shaped cavities 23. The energy absorber would reduce the intensity of low-energy components of the beam, while not significantly affecting the intensity of high-energy components of the beam.

Figure 4:
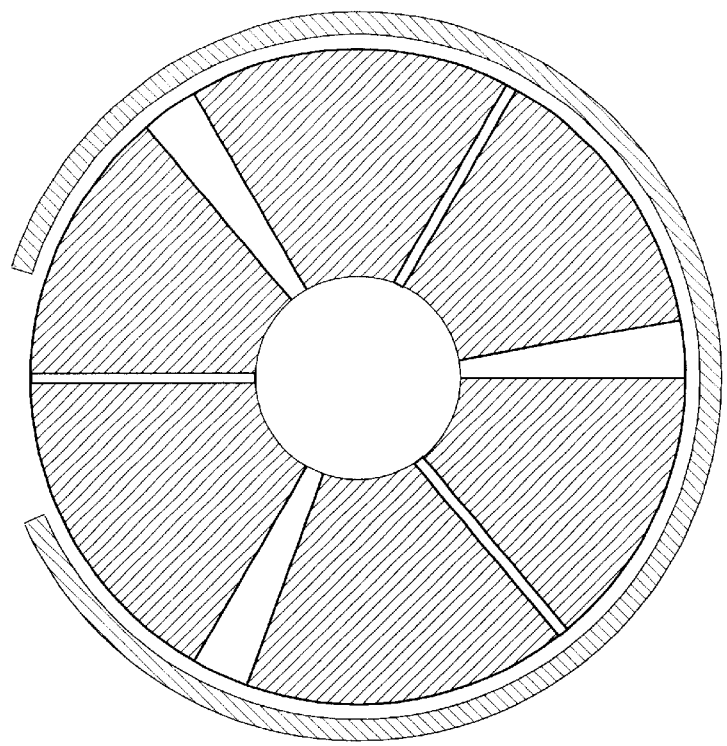
FIGS. 4 and 5 show alternate chopper wheel cavity geometries.
Figure 5:
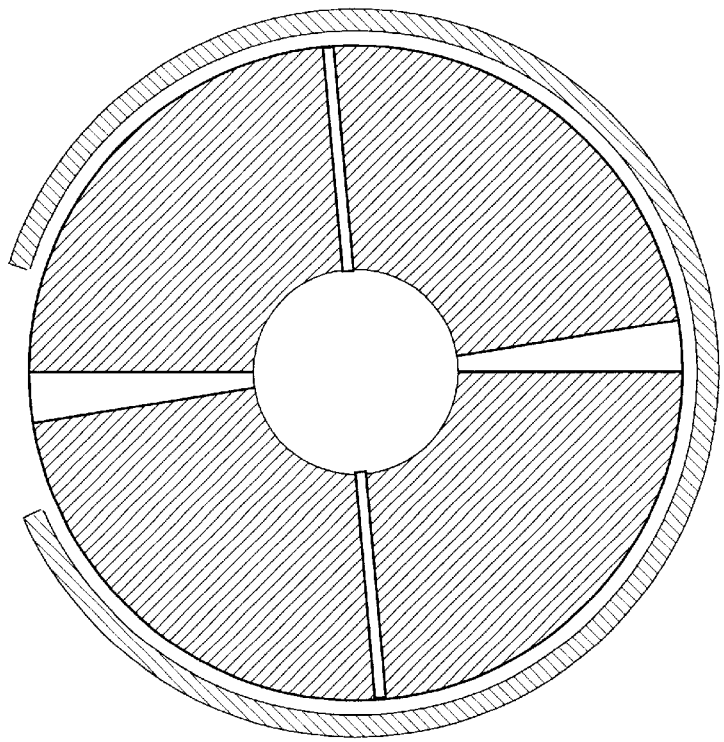

The specific chopper wheel 13 shown in FIG. 3 has four cavities 20—two 60° pie-shaped cavities 23, alternating with two columnar spoke-shaped cavities 22 (of negligible radial size, approximately 3 mm openings). This arrangement produces two fan-shaped beams and two pencil-shaped beams per rotation of the chopper wheel 13. In this arrangement, each beam will have about 60° of rotational sweep. Alternate chopper wheel cavity arrangements are shown in FIGS. 4 and 5. FIG. 4 has six cavities arranged for alternating pencil-shaped beams and fan-shaped beams of approximately 10°, arranged so that each beam will have about 55° of rotational sweep. FIG. 5 is similar to FIG. 4 in producing 10° fan-shaped beams, but in a four cavity arrangement such that each beam sweeps out an angle of about 85°.

Clearly, choosing a specific cavity arrangement involves a compromise between the amount of rotational sweep coverage by the scanning beam 14, and the radial size of the fan-shaped beam. Also, of course, the specific geometry of the chopper wheel 13 needs to be such that only one cavity is aligned with the beam opening 21 at any given time. This ensures that only one scanning beam 14 at a time will be projected out from the chopper wheel 13.

Another embodiment produces an alternating sequence of pencil-shaped and fan-shaped beams without using a chopper wheel arrangement. Instead, a rotating disk may be used having radial slots, the disk rotating in front of a beam opening slit. Wider radial slots will produce a fan-shaped scanning beam 14, while short radial slots produce a pencil-shaped scanning beam 14.

Embodiments also may vary from strict alternation of one beam shape with another. There is no particular reason why such strict alternation would be desired, and it is contemplated that there may be applications in which it is desirable to produce multiple successive scanning beams 14 in one shape, e.g., a pencil-shape, before producing a different shaped scanning beam, e.g., a fan-shape. The chopper wheel geometry that would produce such effects is easily envisioned—having multiple successive columnar spoke-shaped cavities between pie-shaped cavities. The important characteristic is that the different shaped scanning beams lie in the same plane.

Although various exemplary embodiments of the invention have been disclosed, it should be apparent to those skilled in the art that various changes and modifications can be made which will achieve some of the advantages of the invention without departing from the true scope of the invention.

What is claimed is:

1. An inspection system for inspecting an object with penetrating radiation, the system comprising:
   a source of penetrating radiation for providing a beam of radiation, the beam alternating between a first beam shape and a second beam shape, the first and second beam shapes being coplanar;
   a first detector arrangement for detecting penetrating radiation from a portion of the beam transmitted through the object and generating a transmitted radiation signal;
   a second detector arrangement for detecting penetrating radiation from a portion of the beam scattered by the object and generating a scattered radiation signal; and
   a processor for determining at least one characteristic of the object based at least one of the transmitted and scattered radiation signals.

2. The inspection system as set forth in claim 1, wherein the source of penetrating radiation is an x-ray source.

3. The inspection system as set forth in claim 2, wherein the source of penetrating radiation is a pulsed x-ray source.

4. The inspection system as set forth in claim 2, wherein the source of penetrating radiation is an x-ray tube.

5. The inspection system as set forth in claim 2, wherein the source of penetrating radiation is a linear accelerator.

6. The inspection system as set forth in claim 1, further including a rotating chopper wheel that determines the beam shape.

7. The inspection system as set forth in claim 1, further including a rotating disk and slit arrangement that determines the beam shape.

8. The inspection system as set forth in claim 1, wherein the first beam shape is a pencil-shape, and the second beam shape is a fan-shape.

9. The inspection system as set forth in claim 8, further including a collimator for producing the fan shape.

10. The inspection system as set forth in claim 8, further including a scanner arrangement for varying the orientation of the pencil shape with respect to the object.

11. The inspection system as set forth in claim 8, further including an absorber associated with producing the fan-shape beam, the absorber reducing the intensity of low-energy components of the beam, while not significantly affecting the intensity of high-energy components of the beam.

12. The inspection system as set forth in claim 1, wherein the object is in motion with respect to the beam.

13. The inspection system as set forth in claim 1, wherein the system is in motion with respect to the object.

14. A method for characterizing an object, the method comprising:
   illuminating the object with penetrating radiation formed into a beam,
      the beam alternating between a first beam shape and a second beam shape, the first and second beam shapes being coplanar;
   detecting penetrating radiation from a portion of the beam that is transmitted through the object so as to generate a transmitted radiation signal;
   detecting penetrating radiation from a portion of the beam that is scattered by the object so as to generate a scattered radiation signal; and
   determining at least one characteristic of the object based at least on the transmitted and scattered radiation signals.

15. The method as set forth in claim 14, wherein the source of penetrating radiation is an x-ray source.

16. The method as set forth in claim 15, wherein the source of penetrating radiation is a pulsed x-ray source.

17. The method as set forth in claim 15, wherein the source of penetrating radiation is an x-ray tube.

18. The method as set forth in claim 15, wherein the source of penetrating radiation is a linear accelerator.

19. The method as set forth in claim 14, wherein illuminating the object further includes determining the beam shape with a chopper wheel arrangement.

20. The method as et forth in claim 14, wherein illuminating the object further includes determining the beam shape with a rotating disk and slit arrangement.

21. The method as set forth in claim 14, wherein the first beam shape is a pencil-shape, and the second beam shape is a fan-shape.

22. The method as set forth in claim 21, wherein the fan shape is produced by a collimator arrangement.

23. The method as set forth in claim 21, wherein illuminating the object further includes varying the orientation of the pencil shape with respect to the object.

24. The method as set forth in claim 21, wherein the fan-shape beam is produced using an absorber that reduces the intensity of low-energy components of the beam, while not significantly affecting the intensity of high-energy components of the beam.

25. The method as set forth in claim 14, wherein the object is in motion with respect to the beam.

26. The method as set forth in claim 14, wherein the beam is in motion with respect to the object.

\* \* \* \* \*